United States Patent [19]

Combie et al.

[11] Patent Number: 4,473,640

[45] Date of Patent: Sep. 25, 1984

[54] DETECTION OF MORPHINE AND ITS ANALOGUES USING ENZYMATIC HYDROLYSIS

[76] Inventors: Joan D. Combie, 3395 Spangler Dr., #189; Jerry W. Blake, 3214 Montavesta Rd., both of Lexington, Ky. 40502; Thomas E. Nugent, P.O. Box 23075, Lexington, Ky. 40523; Thomas Tobin, 423 Henry Clay Blvd., Lexington, Ky. 40502

[21] Appl. No.: 384,719

[22] Filed: Jun. 3, 1982

[51] Int. Cl.[3] ............................................. C12Q 1/34
[52] U.S. Cl. .................................... 435/18; 435/264; 435/268; 435/803
[58] Field of Search .................... 435/18, 4, 200, 268, 435/269, 264, 274, 803

[56] References Cited

PUBLICATIONS

Fry et al., Clin. Chim. Acta, 51: 183–190, (1974).
Cox, Biochem. J., 71: 763–768, (1959).
Vela et al., Clin. Chem., 14(8): 837–838, (1968).
Levvy et al., Biochem. J., 65: 203–208, (1957).
Stitch et al., Nature, 172: 398–399, (1953).
Dodgson et al., Biochem. J., 55: 253–259, (1953).
Wakabayashi et al., J. Biol. Chem., 236(4): 996–1001, (1961).
Shackleton et al., Clin. Chim. Acta, 21: 105–118, (1968).
Fishman, W. H., Adv. Enzymol., 1955, pp. 361–388.
Dutton, G. J. ed., Glucuronic Acid, Academic Press, pp. 88–116, 301–357, 457–485, 1966.
Yeh, S. Y., J. Pharm. Exp. Therapeutics, 192, 201–210, 1975.
Payte et al., Curr. Ther. Res. 13, 412–416, 1971.
Fish et al., J. Forens. Sci., 19, 676–683, 1974.
Houghton et al., Xenobiotica, 9, 269–279.
Truhaut et al., C. R. Acad. Sc. 1, Paris, Sed D 275, 877–881, 1972.
Predmore et al., J. Forensic Sci., 19(3), 481–489, 1978.

*Primary Examiner*—Esther M. Kepplinger
*Attorney, Agent, or Firm*—Burns, Doane, Swecker & Mathis

[57] ABSTRACT

The invention relates to a method for hydrolyzing drug-glucuronic acid conjugates present in mammalian body fluids, the conjugates being derived from a narcotic analgesic, antagonist, or agonist-antagonist whose metabolism includes conjugation with glucuronic acid. The method comprises incubating the body fluid sample at from about 60° to about 70° C., for at least about 1 hour, with β-glucuronidase derived from *Patella vulgata*, and substantially increases the sensitivity of chromatographic techniques for the detection of morphine and its analogues.

37 Claims, 7 Drawing Figures

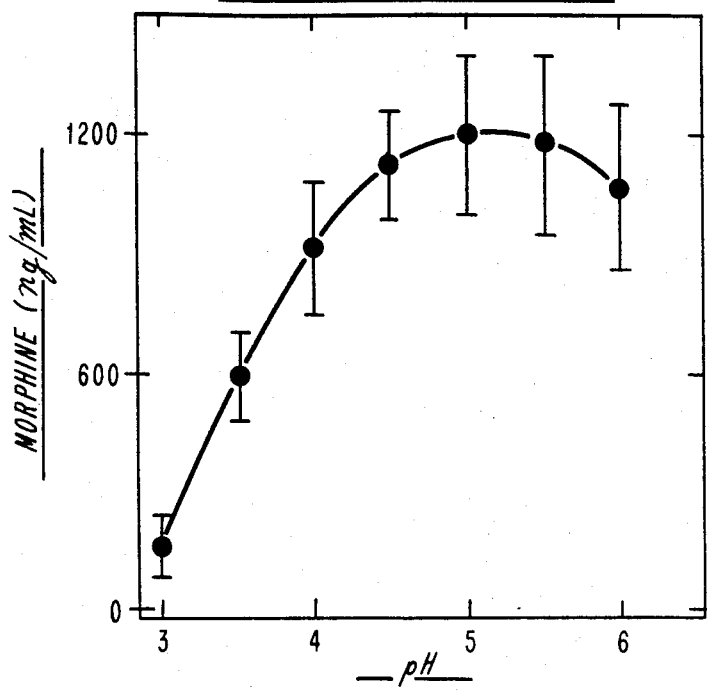
Fig. 1 EFFECT OF pH ON β-GLUCURONIDASE ACTIVITY FROM PATELLA VULGATA
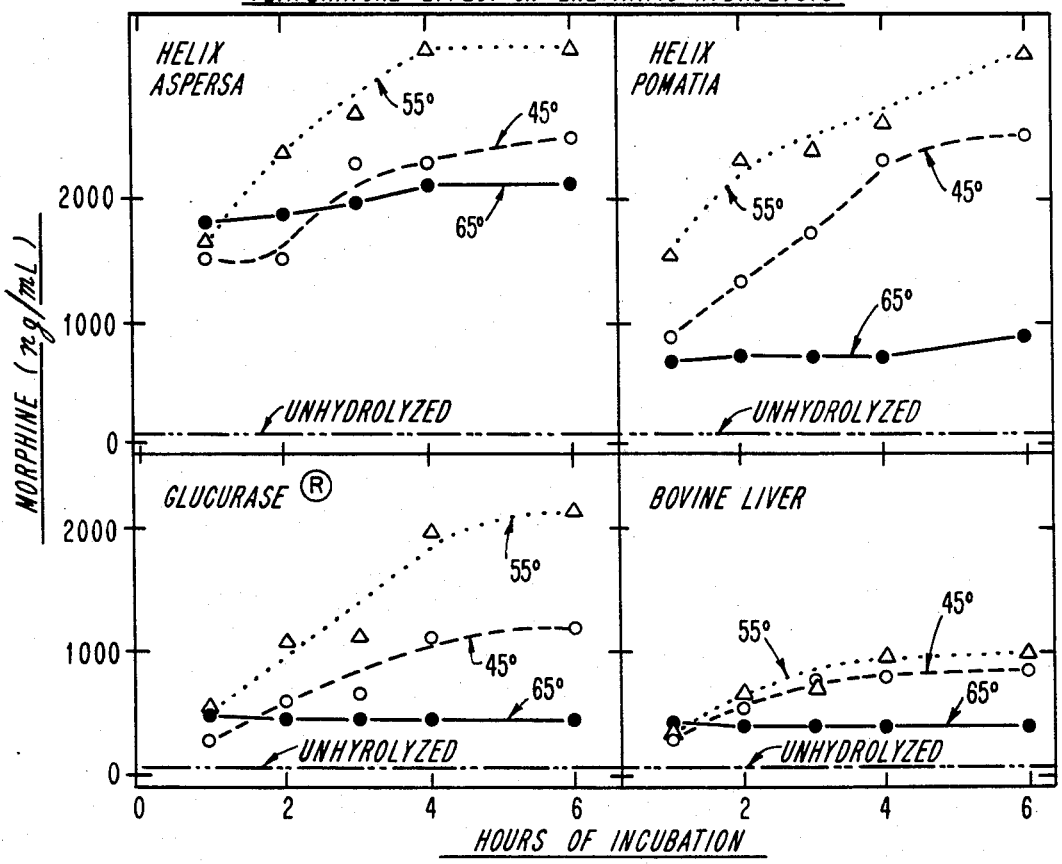
Fig. 2 TEMPERATURE EFFECT ON ENZYMATIC HYDROLYSIS

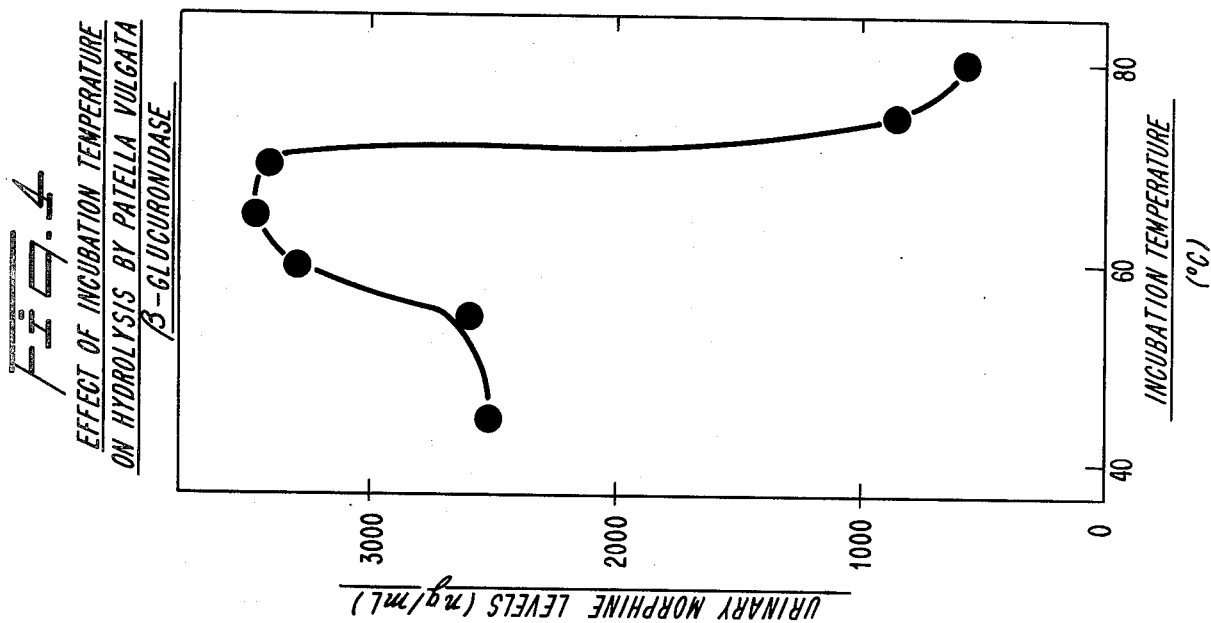
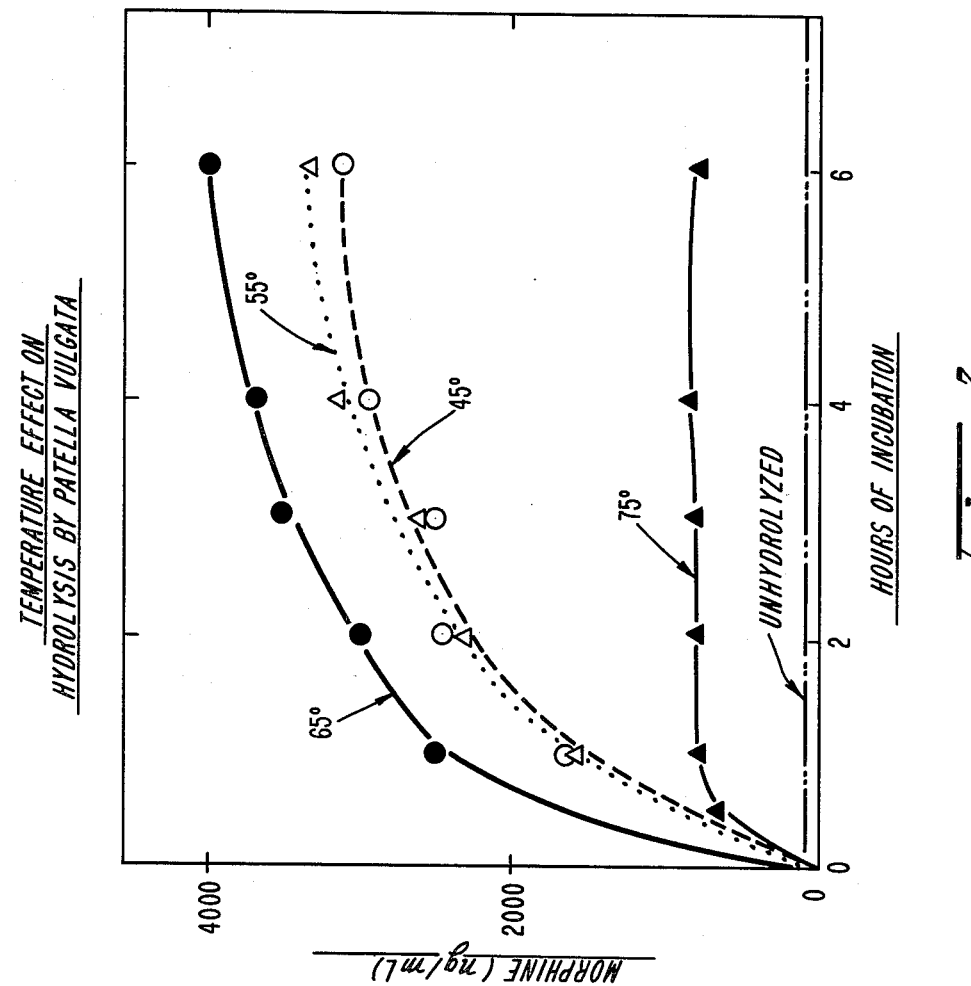

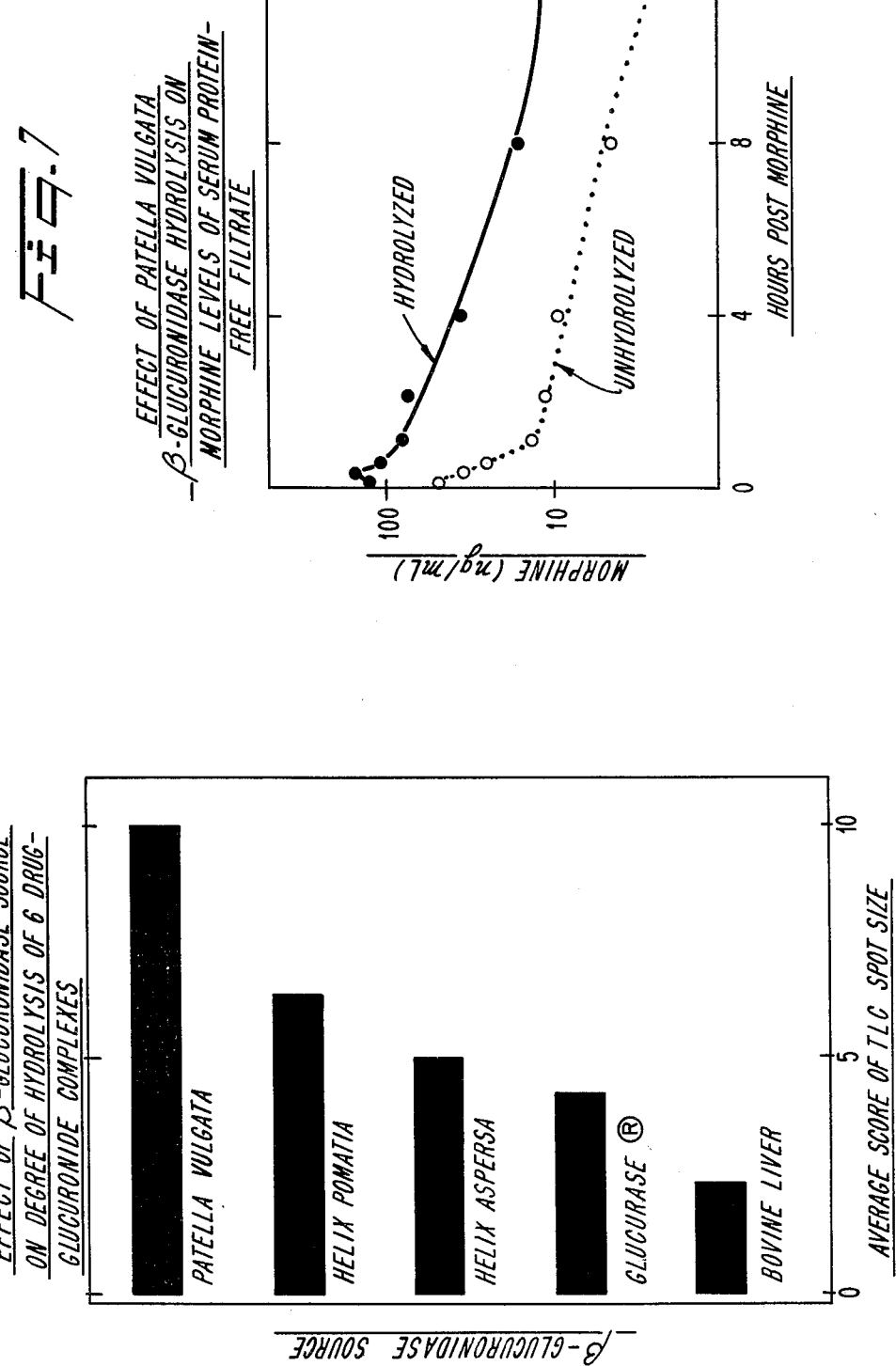

DETECTION OF MORPHINE AND ITS ANALOGUES USING ENZYMATIC HYDROLYSIS

BACKGROUND OF THE INVENTION

1. Field of the Invention

The present invention relates to a method for improving the detection of morphine and its analogues in mammalian body fluids, particularly in equine body fluids, and especially in equine urine and serum protein-free filtrate, utilizing β-glucuronidase from *Patella vulgata* for glucuronide hydrolysis.

2. Background Art

Many drugs, including the narcotic analgesics, are metabolized by conjugation with glucuronic acid (*Glucuronic Acid, Free and Combined*, ed. G. J. Dutton, Academic Press, New York, N.Y., 1966, 88–116, 301–357 and 457–488). In humans, 80–95% of morphine recovered from urine is in the conjugated form [S. Y. Yeh, *J. Pharmacol. Exp. Ther.* 192, 201–210 (1975); E. L. Way et al, *Pharmacol. Rev.* 12, 383–446 (1960)]. The conjugated form is not detected in most assays; however, if the analytical procedure includes hydrolysis, the concentration of detectable morphine in urine can be enhanced. Indeed, J. T. Payte et al, *Curr. Ther. Res.* 13, 412–416 (1971), report that acid hydrolysis of human urine samples increases the sensitivity for detecting morphine by both thin layer and gas-liquid chromatography.

Hydrolysis of the glucuronide metabolite in urine can be performed either with acid or with the enzyme β-glucuronidase. When hydrolysis is used for laboratory analysis it usually is acid hydrolysis, acids being less costly than enzyme preparations and requiring much less time. F. Fish et al, *J. Forens. Sci.* 19, 676–683 (1974), made a detailed study of various conditions for both acid and enzymatic hydrolysis of morphine glucuronide. Those authors found a wide variation in the potency of β-glucuronidase, depending on the source. Overnight incubation of addicts' pooled urine samples at 37° C. using β-glucuronidase from *Escherichia coli*, *Helix pomatia*, *Patella vulgata* and bovine liver resulted in *Escherichia coli* β-glucuronidase consistently exhibiting greatest efficiency (64% of available morphine being liberated under optimal conditions of pH and concentration). Studies of the *E. coli* preparation also were conducted at 60° C. in an effort to reduce the lengthy incubation time, but failed to liberate more than 5% of the available morphine. The authors concluded that the yield obtained from enzyme hydrolysis was disappointing compared to that for acid hydrolysis (which gave 93% yield after 30 minutes); enzyme hydrolysis also required more stringent control of reaction conditions. Moreover, *Escherichia coli* β-glucuronidase, e.g. Sigma Type II employed by Fish et al, is prohibitively expensive for routine laboratory analysis.

There appear to be two reports of enzyme hydrolysis attempted at temperatures higher than about 37° C. which predate Fish et al's work. Cox, *Biochem. J.* 71, 763–768 (1959) reported work done with β-glucuronidase prepared from the visceral humps of the limpet *Cellana tramoserica*. Cox studied the interaction of factors including pH, time, enzyme concentration and temperature on the hydrolysis of phenolphthalein glucuronide, preparatory to a study of the optimum conditions for hydrolysis of enzyme conjugates, and among other findings noted an increase in reaction velocity up to about 60° C., followed by rapid heat-denaturation of the enzyme. Experiments were conducted at 57° C. and 37° C., for 1 hour and 2 hour periods, at enzyme concentrations of 0.1 mg/mL and 0.05 mg/mL, at pH 3.65 to 5.25. Cox apparently did not recognize the possible significance of his elevated temperature work; there do not appear to be reports of his extending his work to hydrolysis of glucuronides other than phenolphthalein glucuronide, or to other enzyme sources. The enzyme source he employed is not commercially available.

Vela et al, *Clin. Chem.* 14, 837–838 (1968) reported one-hour enzymatic hydrolysis using Ketodase (a bovine liver β-glucuronidase product of Sigma) applied to the gas-liquid chromatographic analysis of urinary pregnanolone, pregnanediol and pregnanetriol. The authors indicated that an increase in concentration of Ketodase to 4000 U/ml of urine at pH 4.5 with a 1 hour incubation at 60° C. gave comparable results to those obtained with a 24 hour hydrolysis using 300 U/ml of urine at 37° C. However, Fish et al, as discussed above, in working with morphine glucuronide, were unable to improve results by raising the temperature; indeed, the lengthy incubation time could not be shortened and the results obtained were considerably worse at 60° C. than at 37° C.

The snail, *Helix pomatia*, has been examined as a source of β-glucuronidase by a number of investigators. Shackleton et al, *Clin. Chim. Acta* 21, 105–118 (1968) have reported use of crop fluid from *Helix pomatia* for enzymatic hydrolysis as part of a technique for obtaining a urinary neutral steroid profile analysis in adults and infants. Urine samples were adjusted to pH 5, 0.1 mL of crop fluid was added per 10 mL urine, the mixture was incubated at 37° for 24 hours, an equal quantity of enzyme was added and incubation was continued for a further 24 hours. The authors suggest that enzymatic hydrolysis may be speeded up by increasing the enzyme concentration.

Houghton et al, *Xenobiotica* 9, 269–279, used *Helix pomatia* juice in studies related to the metabolism of anabolic steroids in the horse. Enzyme hydrolysis involved incubating 50 mL urine at pH 5 with 0.25 mL *Helix pomatia* juice for 36 hours at 37° C.; the authors suggest, however, that the hydrolysis may have been incomplete.

Truhaut et al, *C. R. Acad. Sc. Paris, Ser. D* 275, 877–881 (1972), used *Helix pomatia* for enzymatic hydrolysis at 37° for 24 hours; subsequent gas chromatography, both before and after silylation, was then used to detect heroin and its metabolites (e.g. morphine) in the urine of drug addicts.

Predmore et al, *J. Forensic Sci.* 19(3), 481–489 (1978) used acid hydrolysis and enzymatic hydrolysis with *Helix pomatia* obtained from Calbiochem for the recovery of morphine from dog urine. The authors suggest that it may take considerably longer than 16 hours to enzymatically obtain results comparable to acid hydrolysis (about 80% recovery obtained after 40 hours).

A number of investigators have studied the properties of β-glucuronidase obtained from the limpet, *Patella vulgata*. This marine mollusc has been recognized for a number of years as a rich source of both arylsulfatase and β-glucuronidase. Levvy et al, *Biochem. J.* 65, 203–208 (1957), found the visceral hump of this limpet to be exceptionally high in β-glucuronidase activity in comparison with most animal tissues, and indicated that *Patella vulgata* may be one of the best sources of this enzyme for use in the hydrolysis of steroid glucuronides in urine. The authors worked at 0° and 37° C. at various pH's and found the optimum conditions for enzymatic hydrolysis of phenolphthalein glucuronide to be 1 hour at 37° C. and pH 3.8. See also *Glucuronic Acid, Free and Combined,* ed. G. J. Dutton, Academic Press, New York, N.Y., 1966, 301–357; Fishman,*Adv. Enzymol.,* 361–388 (1955); Stitch et al, *Nature* 172, 398–399 (1953); Dodgson et al, *Biochem J.* 55, 253–259 (1953). Dodgson et al, who studied a variety of marine molluscs, reported an optimum pH of 4.0 for *P. vulgata* in p-chlorophenyl-glucuronide substrate, and found that activity of the enzyme preparations increased 7 or 8 times by raising the incubation temperature from 10° to 37.5° C.

Wakabayashi et al, *J. Biol. Chem.* 236, 996–1001 (1961) studied the comparative ability of various β-glucuronidase preparations, namely beef liver, *Escherichia coli, Helix pomatia* and *Patella vulgata,* to hydrolyze certain steroid glucosiduronic acids. The hydrolyses were conducted at 37° C. for 1 hour at various pH levels; then, the time course of hydrolysis for each enzyme preparation and substrate was measured at its optimal pH. No one enzyme preparation was found to be uniquely superior with regard to efficiency of hydrolysis of all substrates studied. Compare Fish et al's more recent comparison of β-glucuronidase from the same four sources in hydrolyzing morphine glucuronide discussed hereinabove.

Not a great deal of work has been done in the past which has utilized hydrolysis of body fluids other than urine in attempting to improve the detection of drugs therein. Berkowitz et al, *Clin. Pharm. and Ther.* 17, 629–635 (1975), have reported acid hydrolysis of whole human serum in an autoclave; conjugated morphine levels were found to be below free morphine levels following intravenous administration until 2 hours post dosing, with a maximum ratio of conjugated to free drug of 3:1. Acid hydrolysis at such elevated temperatures, however, denatures serum proteins, which could trap some of the morphine; such hydrolysis itself may also destroy some of the morphine.

Sensitive and reliable detection, and often quantitation, of morphine and its pharmacologically active analogues are important in many forensic, medical and other laboratory situations, such as in the diagnosis of narcotic abuse (e.g. in connection with parole violation), in investigations into cause of death and in the detection of illegal administration of such compounds in race horses or dogs. Indeed, because the narcotic analgesics and related compounds are often used in equine medicine to control pain and occasionally for their central stimulant actions, the use of these drugs in performance horses is usually prohibited. Unfortunately, the detection and quantitation of morphine and its analogues in equine body fluids, especially urine, are complicated by several factors. In the first place, the dose of drug given to a horse may be relatively small (e.g. 0.1 mg/kg or smaller in the case of morphine). Secondly, equine urine contains large amounts of mucus (from goblet cells in the epithelium and compound tubular glands in the mucous coat of the equine renal pelvis) and glucuronide derivatives of other compounds (e.g. steroids) which further interfere with the recovery of a drug such as morphine or its glucuronide metabolites from horse urine. In fact, urine from a horse is among the most difficult biological fluids in which to reduce contaminants adequately when attempting very sensitive assay methods.

As indicated above, most morphine is excreted bound as the glucuronide. Uncoupling of the morphine from its glucuronide by hydrolysis can, therefore, markedly increase the concentration of detectable morphine, which may be crucial when screening for the low concentration of morphine which may be administered to a horse. (The same would hold true for screening for other narcotics whose metabolism includes conjugation with glucuronic acid.) Moreover, since acid hydrolysis generally increases nonspecific contaminants in specimens [Frey et al, *Clin Chim. Acta* 51, 183–190 (1974)], it would appear that cleavage from the glucuronide would be best achieved enzymatically.

SUMMARY OF THE INVENTION

In view of the foregoing, it is apparent that a serious need exists for an improved method for detecting morphine or an analogue thereof in mammalian body fluids, particularly in equine body fluids, using enzymatic hydrolysis, and it is an object of the present invention to provide such a method. The invention thus provides a method for hydrolyzing drug-glucuronic acid conjugates in a mammalian body fluid sample, the conjugates being derived from a narcotic analgesic, antagonist or agonist-antagonist whose metabolism includes conjugation with glucuronic acid, which method comprises incubating the body fluid sample at from about 60° to about 70° C., for at least 1 hour, with β-glucuronidase derived from *Patella vulgata.* This method substantially increases the sensitivity of chromatographic techniques for the detection of morphine or an analogue thereof in mammalian body fluids, particularly in urine and plasma, and most especially in urine and serum protein-free filtrate.

BRIEF DESCRIPTION OF THE DRAWINGS

FIG. 1 is a plot showing the effect of increasing incubation pH on the amount of urinary morphine (in ng/mL) detected after hydrolysis by β-glucuronidase from *Patella vulgata;*

FIG. 2 is a group of four plots showing the effect on the amount of urinary morphine (in ng/mL) detected after hydrolysis by β-glucuronidase from each of four sources, namely, from *Helix aspersa, Helix pomatia,* Glucurase ® and bovine liver, with increasing incubation time, at three selected incubation temperatures;

FIG. 4 is a plot showing the effect of increasing incubation temperature on the amount of urinary morphine (in ng/mL) detected after hydrolysis by *Patella vulgata* β-glucuronidase;

FIG. 5 is a group of six bar graphs illustrating the ability of β-glucuronidase from each of five sources [*Patella vulgata* (PV), *Helix pomatia* (HP), *Helix aspersa* (HA), Glucurase ® and bovine liver (BL)] to hydrolyze each of six drug-glucuronide complexes (those of apomorphine, butorphanol, hydromorphone, nalbuphine, oxymorphone and pentazocine) in terms of spot sizes on thin layer chromatography (TLC) plates following 1 hour incubation;

FIG. 6 is a bar graph showing the effect of β-glucuronidase source on the degree of hydrolysis of six drug-glucuronide complexes, in terms of average scores of TLC spot sizes; and FIG. 7 is a plot showing the effect of *Patella vulgata* β-glucuronidase hydrolysis on morphine levels of serum protein-free filtrate (in ng/mL).

DETAILED DESCRIPTION OF THE INVENTION

Figure 3:
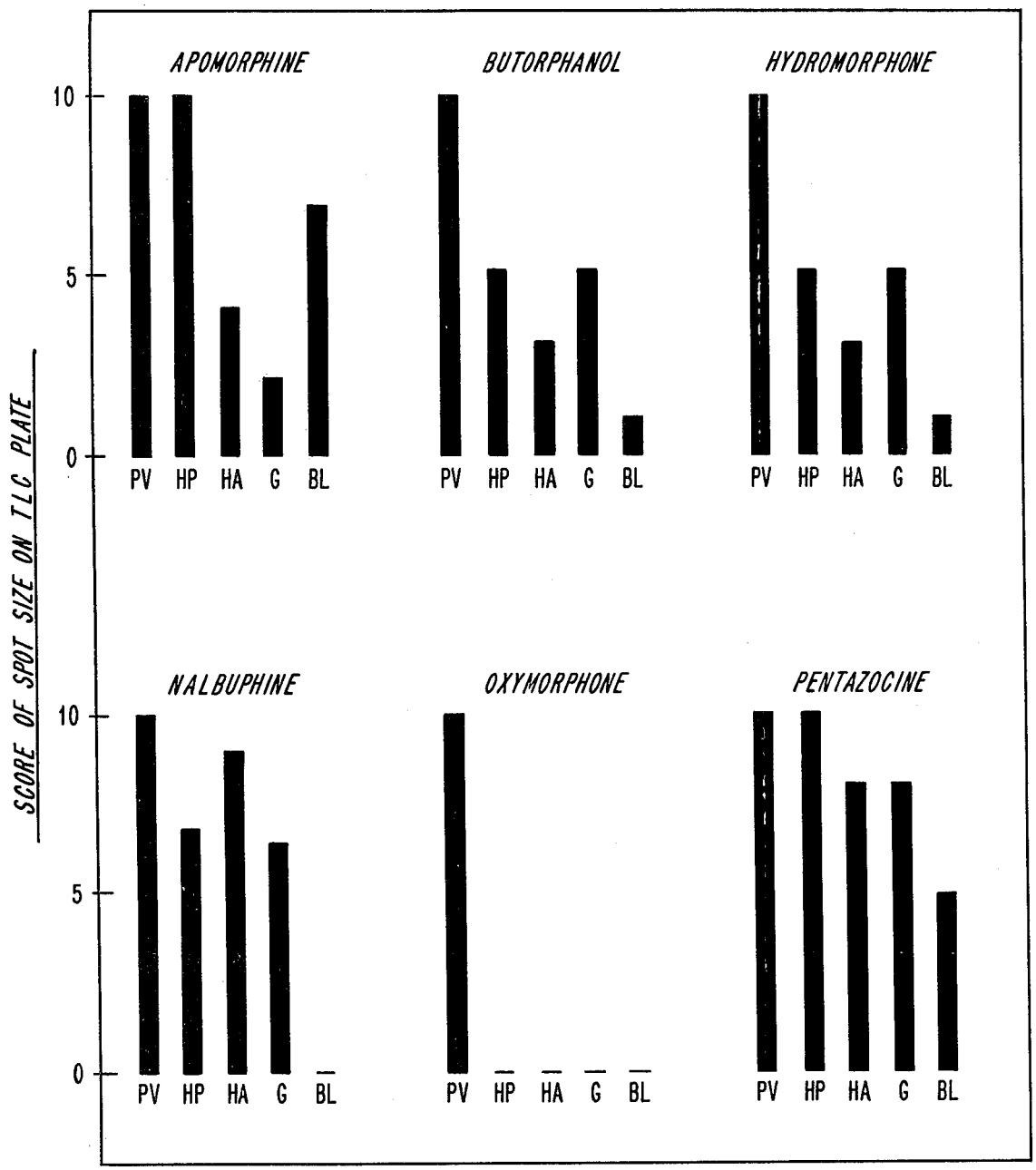
FIG. 3 is a plot showing the effect on the amount of urinary morphine (in ng/mL) detected after hydrolysis with β-glucuronidase from *Patella vulgata,* with increasing incubation time, at four selected incubation temperatures.

*Patella vulgata* β-glucuronidase for use in the present invention can be derived from the common limpet *Patella vulgata* in known manner. See, for example, Levvy et al, *Biochem. J.* 65, 203–208 (1957). Preferably, however, the enzyme is conveniently obtained from a commercial source. *Patella vulgata* Type L-II from Sigma Chemical Co., St. Louis, Mo. 63178 has been found to be particularly useful. This crude lyophilized powder, having β-glucuronidase activity of 1,000,000 to 2,000,000 units per gram solid at pH 3.8 and also having sulfatase activity (inhibited by 0.1 M phosphate), is typically stored in a desiccator at −20° C. Immediately prior to use, the lyophilized sample is weighed and dissolved in distilled, de-ionized water to the desired concentration (e.g. 5000 U/mL) with care to protect both the powdered and reconstituted forms from direct light. It is possible to reconstitute the enzyme extract more in advance of use, but some loss of activity occurs with time and higher storage temperature.

The drugs contemplated for detection in accord with the present invention are narcotic analgesics, antagonists and agonist-antagonists whose metabolism includes conjugation with glucuronic acid. Most of these drugs bear at least one hydroxyl substituent, usually at least one phenolic hydroxyl substituent, which reacts with glucuronic acid in vivo to form the drug-glucuronic acid conjugate (also referred to as the glucuronide or glucuronide complex); hydrolysis of the glucuronide frees the drug, which can then be detected by chromatographic methods, e.g. thin layer or gas-liquid chromatographic techniques. Morphine is a primary example of such a drug.

Nevertheless, it is not necessary for the drug to bear a hydroxyl substituent if the metabolic pathway of the drug includes conversion to a free hydroxy-containing metabolite which then reacts with glucuronic acid in vivo to form a glucuronide complex. Heroin (3,6-diacetylmorphine) is a very well-known example of a drug of this type; two of its major metabolites are 6-monoacetylmorphine and morphine, both of which are conjugated with glucuronic acid in vivo. Thus, for example, analysis of urine samples from heroin addicts ultimately involves detection of morphine present in the samples as a means of determining heroin administration. Note Truhaut et al, *C. R. Acad. Sc. Paris, Ser. D.* 275, 877–881 (1972); Payte et al, *Curr. Ther. Res.* 13, 412–416 (1971).

The drugs contemplated for detection by the instant process thus include morphine and its pharmacologically active analogues which are metabolized by conjugation, directly or via a free hydroxy-containing metabolite, with glucuronic acid to form glucuronides. The term "drug-glucuronic acid conjugates" as used herein is intended to encompass not only glucuronic acid conjugates of the drug actually administered, but also glucuronic acid conjugates of metabolites of the administered drug (whether such metabolites are themselves generally recognized as "drugs" or not). It will be apparent to those skilled in the art that in the case of administration of a drug which must be metabolized to a species that can be conjugated with glucuronic acid, it will be that metabolite which will be freed by hydrolysis according to the invention and ultimately detected, e.g. by chromatographic analysis.

Morphine, which has the structural formula

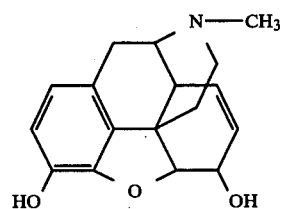

is a potent narcotic analgesic which is principally used to relieve pain; it is also used in the dyspnea of heart failure, in pulmonary edema and cough, as a sedative and in the control of diarrhea (chiefly in the form of a paragoric). Morphine causes both depression and stimulation in the central nervous system and the gut.

The morphine molecule has been subjected to a variety of structural modifications in efforts to enhance selected properties and/or to deemphasize others, as well as to produce drugs which actually antagonize the effects of morphine and other opioid analgesics. Such efforts have led to the development of a variety of classes of chemical compounds, such as the class of morphine analogues whose structures are very closely allied to that of morphine, retaining both the phenolic OH and the N-methyl substituent of morphine, such as levorphanol and oxymorphone, and which as a group have strong analgesic, respiratory depressant and smooth muscle-affecting activity but which also are highly addicting. Retention of the phenolic hydroxyl while replacing the methyl on the nitrogen atom with a larger alkyl or similar side-chain has afforded both morphine analogues which are relatively pure opioid antagonists (e.g. naloxone and naltrexone) and are used in the treatment of narcotic-induced respiratory depression (overdose), in the diagnosis of narcotic addiction and in the prophylaxis of narcotic abuse; and morphine analogues which are agonist-antagonists (e.g. buprenorphine, pentazocine, nalorphine and cyclazocine), which display varying degrees of morphine-like activity as well as of morphine-antagonist behavior, and which can therefore be used as analgesics as well as for the purposes for which the relatively pure antagonists are used. In the horse, many of these drugs are used for their central stimulant actions.

Yet other structural modifications of the morphine molecule have resulted in codeine and its analogues; methadone and related compounds; and meperidine and related compounds such as profadol. Also see, generally, *Pharmacological Basis of Therapeutics*, ed. Goodman and Gilman, sixth edition, Chapter 22, "Opioid Analgesics and Antagonists", by Jaffe and Martin, pp. 494–534 (MACMILLAN PUBLISHING CO., INC., New York, 1980); *Cutting's Handbook of Pharmacology*, sixth edition, ed. T.Z. Czáky, M.D., Appleton-Century-Crofts/New York, Chapter 50, pp. 551–571.

Particularly significant morphine analogues contemplated by the present invention include morphine-like analgesics such as hydromorphone, levorphanol, heroin, codeine, etorphine, metopon and oxymorphone; and narcotic antagonists and agonist-antagonists such as buprenorphine, diprenorphine, butorphanol, cyclazocine, pentazocine, phenazocine, levallorphan, nalorphine, naloxone, alazocine, nalbuphine, oxilorphan, nalmexone and naltrexone. Other analogues contemplated by the invention include ketobemidone, apocodeine, profadol, cyclorphan, cyprenorphine, apomorphine, desomorphine, dihydromorphine, 3-hydroxy-N-methylmorphinan, levophenacylmorphan, metazocine, norlevorphanol, phenomorphan, pholcodine and hydroxypethidine.

The structural formulae for representative morphine analogues contemplated by the present invention are set forth below:

etorphine
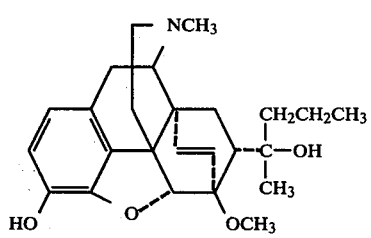

diprenorphine
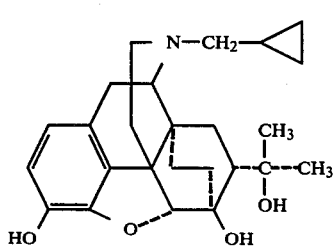

hydromorphone
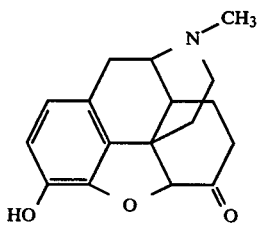

heroin
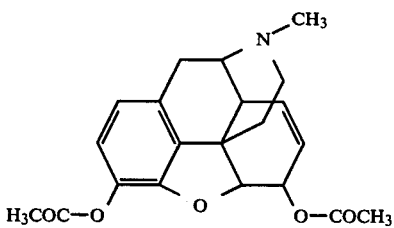

apomorphine
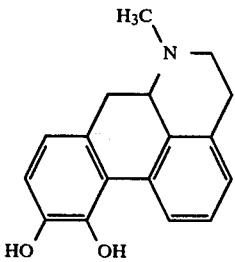

levorphanol
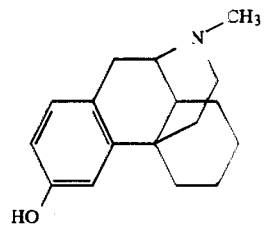

oxymorphone
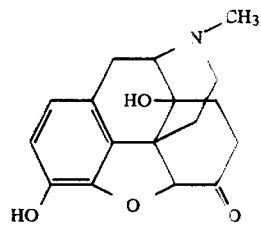

buprenorphine
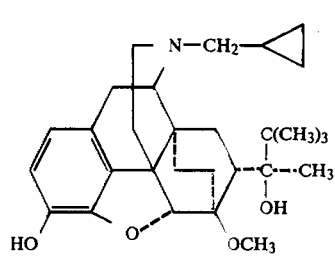

butorphanol
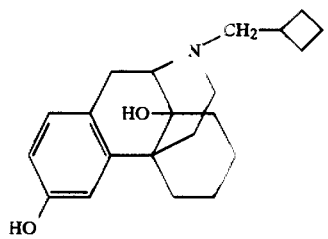

cyclazocine
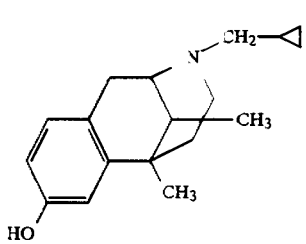

pentazocine
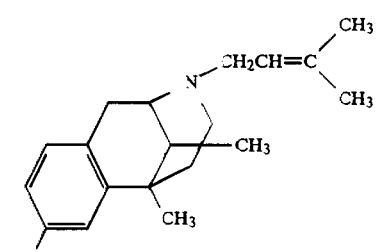

phenazocine
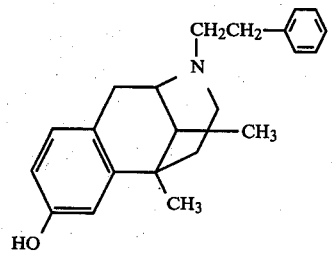

nalorphine
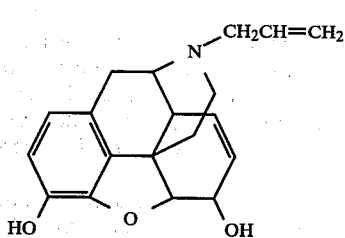

levallorphan
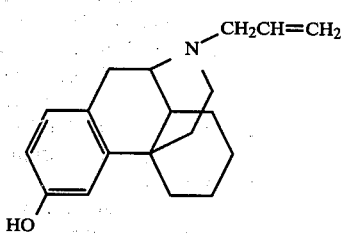

naloxone
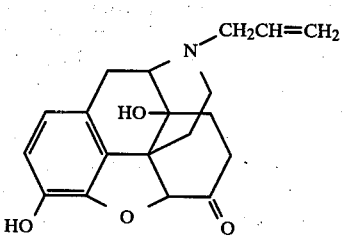

nalbuphine
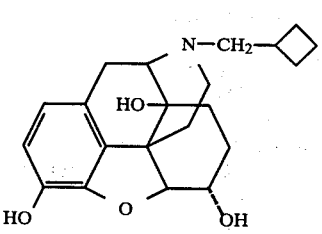

naltrexone
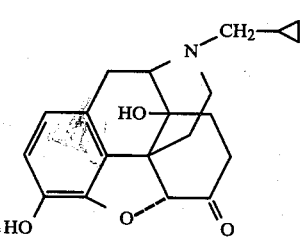

codeine
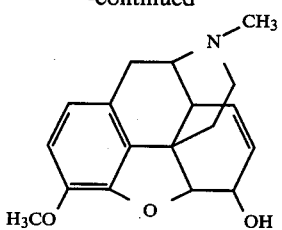

At the present time, morphine, apomorphine, butorphanol, hydromorphone, nalbuphine, oxymorphone, pentazocine, etorphine, diprenorphine, nalorphine, levorphanol, buprenorphine and heroin are compounds whose detection in the horse in accord with the instant invention is of particular interest.

In accord with the present invention, it has now been surprisingly found that *Patella vulgata* β-glucuronidase can be advantageously employed for hydrolysis of mammalian body fluid samples at a temperature of from about 60° to about 70° C., preferably of 65° C., which are far warmer conditions than the commonly used 37° C. The sea coast habitat of the common limpet would not lead one to expect the presence of such a temperature-resistant enzyme.

Because of the high activity found for *Patella vulgata* β-glucuronidase at the high temperature just mentioned, it has been found that the incubation period can be considerably shortened from the times commonly reported in the literature. A time period for incubation of at least about 1 hour is generally recommended, usually from about 1 to about 6 hours, preferably from about 1 to 3 or 1 to 4 hours. An about one-hour incubation is often highly satisfactory if only qualitative results are needed, the hydrolysis being about 60% complete after that length of time. However, an approximately three-hour incubation is considered optimum and allows quantitation of the drug administered. Increasing the incubation time beyond about 3 hours does not greatly increase the amount of drug liberated. These short times make the instant enzymatic hydrolysis much more useful for routine laboratory testing than was the case in the past. Preferably, the commercial lyophilized *P. vulgata* powder is combined with water to form a solution having 5000 U of β-glucuronidase per mL and then is preferably employed in an equal volume with the sample to be analyzed. A pH range of 4.5 to 5.5 is generally preferred, with pH 5 being optimal. Also, while 5000 U of enzyme per mL of body fluid is highly acceptable, higher or lower enzyme concentrations may be selected depending on other process variables such as the particular incubation time and temperature employed and the suspected concentration of glucuronide in the sample to be analyzed.

It has recently been found that the addition of 5000 U of bovine liver β-glucuronidase per mL of equine urine enabled increased detection of morphine in the urine for up to about 120 hours after horses were intravenously dosed with 0.1 mg of morphine/kg of body weight, although total urinary excretion of morphine and its glucuronide peaked at 1–2 hours after dosing [Combie et al, *Am. J. Vet. Res.* 42, 1523–1530 (1981)]. Combie et al further found that the ratio of the amount of morphine released by β-glucuronidase to the amount of free morphine in the urine is dependent on the time elapsed from drug administration, increasing steadily to a peak at 9 hours after dosing. While hydrolysis with *P. vulgata*

β-glucuronidase in accord with the present invention is described below for urine samples obtained from 50 minutes to 12 hours after dosing, it is apparent that the instant hydrolysis should improve detection of morphine and its analogues even in urine samples obtained at considerably longer periods after drug administration, e.g. up to about 120 hours, with at least about a threefold increase being obtained for samples taken up to about 96 hours after administration.

The optimum amount of time after administration at which to obtain fluid samples of course will vary with the particular fluid selected for analysis, as well as the route of administration of the drug and even with the particular species of animal and drug involved. It has been found, for example, that intravenous dosing of horses with morphine results in high blood levels of conjugated morphine within a few minutes after dosing; between 5 minutes and 12 hours post dosing, hydrolysis in accord with the present invention of serum protein-free filtrate has been found to result in an average 4.9-fold increase in free morphine levels. Little or no morphine glucuronide was observed 48 hours after dosing.

As obtention of urine samples is frequently more convenient then obtaining samples of other body fluids, it is expected that urine samples will most often be selected for hydrolysis according to this invention. However, the applicability of the instant process to other fluids, especially serum, is very important in certain situations, e.g. in analysis of pre-race equine blood samples, in post-mortem analysis, etc.

Although it is possible to hydrolyze protein-containing body fluids such as blood or plasma samples in accord with the present invention, proteins present in these samples will coagulate at the approximately 60° to 70° C. incubation temperature utilized herein. Such coagulation could trap some of the drug to be detected; it also makes the sample much more difficult with which to work. Therefore, in order to obtain optimum results, proteins are best removed from such body fluid samples prior to incubation (unless lower incubation temperature and longer incubation time are utilized). A preferred method of removing proteins which is illustrated hereinafter employs centrifugation of equine serum in commercially available filters to remove materials having molecular weights above 50,000. The resultant filtrate is considered to be protein-free, although a small percentage of protein may be present therein. If desired, a finer filter such as one designed to remove materials having molecular weights above 25,000 could be used to further reduce the amount of protein left in the serum. Also, there are many alternate methods known for preparing protein-free filtrates which could be employed, e.g. addition of acid to the sample to precipitate the protein, or addition to the sample of a solvent capable of precipitating protein. Such pretreatment of samples to remove protein is unnecessary in the case of urine.

In order to illustrate more fully the characteristics and advantages of the present invention, the following experimental procedures and results are given. However, it is to be understood that the description below is by way of illustration only and is not to be construed as limiting the invention either in spirit or in scope as many modifications both in materials and in methods will be apparent to those skilled in the art. In the description below as well as in the foregoing discussion, the abbreviation "U" has been employed to designate Fishman Units, a well-known measurement for enzymatic activity.

MORPHINE GLUCURONIDE EXPERIMENTS

Materials and Methods

For all analyses, a Model 3700 gas chromatograph equipped with a $^{63}$Ni electron-capture detector (Varian Instruments, Sunnyvale, Calif. 94086) was used. The detector was operated at 290° C. Separations were done on a 1.8 m×2 mm siliconized glass column packed with SP 2250-DB on 100/120 Supelcoport (Supelco, Inc., Bellfonte, Pa. 16823). Column oven temperature was maintained at 235° C. and injection port temperature at 250° C. The flow rate of the carrier gas, pre-purified nitrogen, was 30 mL/minute.

Thoroughbred and standardbred mares, eight to 22 years old, were kept at pasture except on the day of an experiment, when they were housed in box stalls. Drugs were administered intravenously into the left jugular vein. Urine samples were collected by bladder catheterization.

β-Glucuronidase from five sources [*Patella vulgata* (Type L-II), *Helix aspersa* (Type HA-4), *Helix pomatia* (Type H-1), bovine liver (Type B-3), and Glucurase ®] was obtained from Sigma Chemical Co., St. Louis, Mo. 63178. All except the Glucurase ® were lyophilized powders. The enzyme from *H. pomatia* and *H. aspersa* was partly purified, while that from *P. vulgata* was a crude powder. Glucurase ®, a bovine-liver β-glucuronidase solution in acetate buffer, pH 5, was stored at 4° C. The four lyophilized preparations were stored in a desiccator at −20° C.

Dichloromethane and ethyl acetate were of "OmniSolve" purity (MCB Manufacturing Chemists, Inc., Cincinnati, Ohio 45246). Pentafluoropropionic anhydride (Pierce Chemical Co., Rockford, Ill. 61105) was stored at 4° C. Morphine sulfate injectable was obtained from Eli Lilly Co., Indianapolis, Ind. 45206. The 1.5 mol/L carbonate buffer was prepared by adding a 186 g/L solution of $NaCO_3 \cdot H_2O$ to 500 mL of water containing 63 g of $NaHCO_3$ until the pH was 8.9.

Horses were dosed with 0.1 mg of morphine per kilogram body weight. Urine samples were collected 6 or 12 hours later except in the temperature-effect work, for which samples were collected 50 minutes after dosing. The samples were stored in polystyrene containers at −20° C. until analyzed.

Immediately before an experiment, the lyophilized β-glucuronidase samples were weighed and dissolved in distilled, de-ionized water, with care to protect both the powdered and reconstituted forms from direct light. For the stability study, the reconstituted *P. vulgata* enzyme was stored at 4° C. for the duration of the experiment. The Glucurase ® solution was used as obtained from the manufacturer.

Typically, after urine samples were adjusted to the desired pH with glacial acetic acid, 100 μL of urine, 100 μL of enzyme solution, and 50 μL of water were incubated in 1-mL sealed, glass ampules in a waterbath. After hydrolysis, 50 μL of the solution was analyzed as detailed by Combie et al, *Am. J. Vet. Res.* 42, 1523–1530, (1981). The urine, adjusted to pH 8.9 by adding 0.5 mL of the carbonate buffer, was extracted with 4 mL of dichloromethane/isopropanol (9/1 by volume) and centrifuged, and the organic phase was allowed to drip through silica gel (Silic AR ® CC-7 Special) columns. The columns were washed with five 2-mL aliquots of ethyl acetate/methanol/glacial acetic acid (8/1/1 by volume). Morphine was eluted from the columns with 2 mL of ammonia water (2 drops NH₄OH per milliliter of water) and extracted into 4 mL of dichloromethane/isopropanol (9/1 by volume). The solvent was transferred into 15-mL conical glass tubes and evaporated under a stream of nitrogen. The morphine was derivatized by adding 25 μL of pentafluoropropionic anhydride to the residue. The capped tubes were incubated for 25 minutes at 65° C. Excess reagent was then evaporated under a stream of nitrogen. The residue was redissolved in 25-200 μL of ethyl acetate and a 2-μL aliquot was injected into the gas chromatograph. The retention time for the derivatized morphine was approximately 1.6 minutes.

RESULTS AND DISCUSSION

β-Glucuronidase from the five sources was examined for optimum conditions for hydrolysis of morphine glucuronide in equine urine.

The first variable studied was pH. Each urine sample collected 12 hours after dosing was incubated for 24 hours with (per milliliter of sample) 5000 U of β-glucuronidase from each of the five sources at different pH values. FIG. 1 shows an example of the series of pH vs activity curves, in terms of morphine released. In each case, variation of pH by 0.5 unit on either side of the optimum made no significant difference in free morphine yield. Table 1 below compares the instant results with the manufacturer's recommended pH, as determined by the activity of the enzyme on phenolphthalein glucuronide. The only significant difference was for *P. vulgata*, for which the recommended pH was 3.8, as compared with pH 5, which as can be seen from FIG. 1, gave the highest yield of free morphine in the present tests.

TABLE 1

| β-Glucuronidase source | Optimum pH for phenolphthalein glucuronide hydrolysis | Optimum pH for morphine glucuronide hydrolysis |
|---|---|---|
| Patella vulgata | 3.8 | 5.0 |
| Helix aspersa | 5.0 | 4.5 |
| Helix pomatia | 5.0 | 4.5 |
| Glucurase ® | 5.0 | 5.5 |
| Bovine liver | 5.0 | 5.0 |

After optimum pH's were determined, β-glucuronidase from each source was incubated with urine samples for 24 hours at 37° C. at the optimum pH for each preparation. It was found that the preparations differed substantially in their ability to free morphine from its glucuronide conjugate. Five thousand units (U) of β-glucuronidase from *P. vulgata* released an average of 1205 ng of morphine per milliliter of urine; under the same conditions, *Helix aspersa* β-glucuronidase freed 965 ng, *Helix pomatia* 893 ng, Glucurase ® 949 ng and bovine liver 320 ng. Enzyme preparations which were effective in 5000 U concentration were not found to be substantially more effective at 25000 U; for example, for the *P. vulgata* preparation, increasing the amount of β-glucuronidase from 5000 to 25000 U increased the yield by only 10%. In contrast, an initial poor activity such as that exhibited by the bovine liver extract was increased dramatically, about three times more morphine being freed when the enzyme concentration was quintupled. (Use of such large amounts of reagent is, however, prohibitively expensive when screening large numbers of samples on a daily basis.)

FIGS. 2 and 3 show the effect of temperature on reaction rate and yield of free morphine. Urine collected 50 minutes after dosing with morphine was adjusted to the optimal pH for each enzyme preparation and incubated with 5000 U of β-glucuronidase per milliliter of urine. For all enzyme preparations except *P. vulgata*, 55° C. was found to be the optimum temperature. Generally, the rate of reaction had begun to level off by 4 hours. Assuming that a 120 hour incubation at 35° C. would give a 100% yield of free morphine, after a 6 hour incubation at 55° C., the reaction of the enzyme preparation from *H. pomatia* was 99% complete, 89% for *H. Aspersa*, 61% for Glucurase ® and 36% for bovine liver. The enzyme from *P. vulgata* was able to withstand 65° C., but its activity was attenuated at 75° C. FIG. 4 illustrates the temperature ranges within which *P. vulgata* liberates the most morphine.

Because in general the reaction rate will double with each 10° C. increase in temperature, a reaction will arrive at the same endpoint in half the time if the temperature is increased by 10° C. (up to the point at which the enzyme is denatured by too high temperatures). The ability of *P. vulgata* β-glucuronidase to give highest yields of morphine at 10 degrees higher than the temperature at which the other enzyme preparations have been found to function effectively (and very substantially higher than the 37° C. temperature commonly used in the past), substantially shortens the incubation time. After a 3 hour incubation at 65° C. of urine with the enzyme from *P. vulgata*, the urine was found to contain 35-fold more free morphine than without hydrolysis. Assuming incubation at 35° C. for 120 hours gives 100% recovery of free morphine, in the case of the *P. vulgata* enzyme the proportion of free morphine recovered was found to be essentially the same for incubation at 35° C. for 24 hours, as for 45° C. for 12 hours, 55° C. for 6 hours, or 65° C. for 3 hours. Table 2 below shows the amount of morphine liberated from equine urine incubated with the *Patella vulgata* β-glucuronidase preparation at 65° C., as a function of incubation time.

TABLE 2

| Effect of Incubation Time on Morphine Liberated by *P. Vulgata* at 65° C. | |
|---|---|
| Incubation Period (hours) | Morphine (ng/ml) |
| 1 | 2505 |
| 2 | 2982 |
| 3 | 3491 |
| 4 | 3674 |
| 6 | 3957 |

Table 3 lists the 1981 cost of β-glucuronidase from each source for the analysis of 0.5 mL of urine, based on 5000 U of enzyme per milliliter of urine and the amount of morphine liberated from 1 mL of urine after a 24 hour incubation at 37° C. From these data, a cost-effect ratio was calculated. The enzyme preparation from *P. vulgata* cost 6.7¢ to release 1 μg of morphine from its glucuronide; 33.1¢ worth of bovine-liver extract was needed to hydrolyze the same amount of morphine glucuronide.

TABLE 3
Cost-Effect Ratios of Hydrolyses

| $\beta$-Glucuronidase source | Cost/tube, ¢ | Morphine, mg/L | Cost-Effect ratio, ¢/μg |
|---|---|---|---|
| Patella vulgata | 8.1 | 1.205 | 6.7 |
| Helix aspersa | 7.5 | 0.965 | 7.8 |
| Glucurase ® | 20.0 | 0.949 | 21.1 |
| Helix pomatia | 10.6 | 0.734 | 14.4 |
| Bovine liver | 10.6 | 0.320 | 33.1 |

To ascertain the stability of the reconstituted enzyme extract from *P. vulgata*, a 5000 U/mL solution of same in distilled, de-ionized water was stored at 4° C., using aliquots of this solution for analyses of a split sample (stored at −20° C.) on successive days. No change in enzyme activity was observed for the first 48 hours, but by six days after reconstitution, the enzyme released 9.8% less morphine than on the first day.

There was no difference in enzyme activity among batches of lyophilized *P. vulgata* $\beta$-glucuronidase stored at −20° C. in a desiccator for seven months, three months, or two weeks.

There are substances naturally present in urine that either interfere with or inhibit the activity of $\beta$-glucuronidase. A specific $\beta$-glucuronidase inhibitor known to occur in human urine, saccharo-1,4-lactone, and another possible interference, sulfate ions, were removed [according to the procedure of Shackleton et al, *Clin. Chim. Acta* 21, 105–118 (1968)] in an unsuccessful attempt to reduce the amount of enzyme required. Shackleton et al's work was done with human urine; the $\beta$-glucuronidase inhibitors in equine urine may be different, or equine urine may have other glucuronides competing for the available enzyme.

Enzyme activators, including NaCl and bovine serum albumin, were checked for their ability to increase the free morphine yield, but no significant improvement was noted.

EXPERIMENTS WITH MORPHINE ANALOGUES

Investigation of the action of five sources of $\beta$-glucuronidase enzymes on the hydrolysis of glucuronides of apomorphine, butorphanol, hydromorphone, nalbuphine, oxymorphone and pentazocine in equine urine was undertaken.

Materials and Methods

Experiment 1

Six mares were dosed intravenously (IV) with one of the following:

(a) 0.012 mg apomorphine hydrochloride (Eli Lilly & Co., Indianapolis, Ind.) per kg;
(b) 0.05 mg butorphanol tartrate (Stadol ®, Bristol Laboratories, Syracuse, N.Y.) per kg;
(c) 0.01 mg hydromorphone hydrochloride (Wyeth Laboratories, Inc., Philadelphia, Pa.) per kg;
(d) 0.14 mg nalbuphine hydrochloride (Nubain ®, Endo Laboratories, Inc., Garden City, N.Y.) per kg;
(e) 0.005 mg oxymorphone hydrochloride (Numorphan ®, Endo Laboratories, Inc., Garden City, N.Y.) per kg; and
(f) 0.25 mg pentazocine lactate (Talwin-V ®, Winthrop Laboratories, New York, N.Y.) per kg.

A urine sample was obtained 75 minutes later by bladder catheterization from the horse dosed with oxymorphone. Urine samples were obtained from the other five horses 50 minutes after dosing.

Five sources of $\beta$-glucuronidase were obtained from Sigma Chemical Co., St. Louis, Mo.: *P. vulgata* (Type L-II), *Helix aspersa* (Type HA-4), *Helix pomatia* (Type H-1), bovine liver (Type B-3) and Glucurase ®. The first four were lyophilized powders stored at −20° C. which were weighed out and dissolved in distilled, de-ionized water to make solutions equivalent to 5000 U of $\beta$-glucuronidase per mL immediately before an assay was run. Glucurase ® was a bovine liver $\beta$-glucuronidase solution, acetate buffered to pH 5 and stored at 4° C. It was used as obtained from the manufacturer. Urine samples to be hydrolyzed by either *H. aspersa* or *H. pomatia* were adjusted to pH 4.5; those to be hydrolyzed by *P. vulgata* or bovine liver were brought to pH 5; and those to be incubated with the Glucurase ® were adjusted to pH 5.5 with acetic acid.

Hydrolysis was performed by mixing 200 μL of urine from each horse, except the one given oxymorphone, with 200 μL of each enzyme solution and incubating for 1 hour in 1 mL sealed, glass ampules in a water bath. For oxymorphone, 400 μL of urine and an equal volume of enzyme were incubated. An incubation temperature of 65° C. was used for samples containing *P. vulgata* as the $\beta$-glucuronidase source, while all other samples were incubated at 55° C.

Following incubation, 200 μL of the urine-$\beta$-glucuronidase mixture (600 μL for samples containing oxymorphone) were mixed with 500 μL of a 1.5 M carbonate buffer, bringing the pH to 8.9 with the exception of urine from the horse dosed with apomorphine. Urine containing apomorphine was adjusted to pH 7. The buffered urine samples were extracted with 4 mL dichloromethane:isopropanol (9:1 by volume). Following separation by centrifugation, the solvent was transferred to clean tubes and 1 mL of 0.1 N $H_2SO_4$ was added to each. The tubes were mixed gently for 15 minutes. The layers were separated by centrifugation and the solvent was discarded. Two mL of the carbonate buffer were added to each tube, bringing the pH to 8.9, except for apomorphine-containing samples. For samples from horses dosed with apomorphine, only 0.5 mL of the buffer was added to adjust the pH to 7. Four mL of fresh solvent were added to each tube. Following extraction and separation by centrifugation, the dichloromethane:isopropanol solution was transferred to a clean set of tubes and evaporated to dryness under a stream of nitrogen.

The residue was redissolved in 25 μL of dichloromethane and spotted on high performance thin layer chromatography (TLC) plates (Brinkman Instruments, Inc., Westbury, N.Y.; E. Merck, manufacturer) precoated with silica gel 60, using long capillaries drawn from 22.9 cm Pasteur pipettes. The plates were developed in ethyl acetate:methanol:glacial acetic acid (80:10:10 by volume). The solvent front was allowed to traverse a distance of 5 cm. Following air drying, the plates were sprayed with modified Folin-Denis reagent. [A mixture of 10 g sodium tungstate, 2 g 12-molybdosilicic acid, 5 mL concentrated phosphoric acid and 50 mL water was refluxed for 2 hours. The mixture was diluted to 100 mL with additional water and stored at 0°–5° C. (can be stored at room temperature).] The plates were then exposed to fumes of ammonium hydroxide to maximize the blue-green color reaction.

The plates were labeled with a code unknown to the person reading them. A score of 10 was assigned to the largest, most distinct spot for each drug. Failure to detect the presence of a drug was recorded as a zero. The other spots were then ranked on this 0 to 10 scale by the independent reader.

Experiment 2

Six mares were dosed with saline for the control part of this experiment and on a separate occasion were given 0.4 mg furosemide (Lasix ®, National Laboratories Corp., Somerville, N.J.) per kg for the test section of this experiment. This was done in random order. The time of administration of the saline or the diuretic was set as −4 hours, corresponding to 4 hours before hypothetical race time. Water was withheld at this time. Each horse was given one of six drugs in the same dosages as listed in Experiment 1. The timing of this drug administration ranged from 20 to 45 minutes before post-time, as listed in the Table below.

TABLE

| Experimental Design | |
|---|---|
| −4 hours | adminstered saline (control) or 0.4 mg furosemide/kg; water withheld. |
| −45 minutes | administered nalbuphine, oxymorphone, pentazocine. |
| −30 minutes | administered butorphanol, hydromorphone. |
| −20 minutes | administered apomorphine. |
| 0 minute | POST TIME (hypothetical). |
| +20 minutes | allowed water ad libitum. |
| +30 minutes | urine sample collected. |
| +1 hour | urine sample collected. |
| +2 hours | urine sample collected. |

Twenty minutes after post time, water buckets were returned to the stalls housing these horses and they were allowed water ad libitum for the duration of the experiment. Urine samples were collected by bladder catheterization at 30 minutes, 1 hour and 2 hours after the time of the hypothetical race. Samples were stored at −20° C. until they could be assayed. The specific gravity of all samples was determined.

Urine samples were adjusted to pH 5. Either 80 μL or 500 μL of urine were incubated with an equal volume of a 5000 U/mL solution of β-glucuronidase from *P. vulgata* for 3 hours at 65° C. The hydrolyzed urine samples were assayed as outlined under Experiment 1. The samples were assigned a number with the aid of a random number generator. The plates were read and scored by a reader who had no knowledge of either the code or the experimental design. A score of 10 was given for the largest, most distinct spots for the entire experiment. Failure to detect the presence of a drug was assigned a zero and other spots were ranked on this 0 to 10 scale.

Results and Discussion

The ability of β-glucuronidase from five sources to hydrolyze six different drug-glucuronide complexes is shown in FIG. 5. For all six drugs, hydrolysis by the *P. vulgata* preparation gave the maximum size spot on the TLC plate and was assigned a score of 10. With the exception of apomorphine, use of β-glucuronidase from powdered bovine liver resulted in the lowest score, indicating that for five of the drugs in this study, the bovine liver preparation had the poorest ability to hydrolyze the drug-glucuronide complex. β-Glucuronidase from *H. pomatia, H. aspersa* and the Glucurase ® solution gave intermediate results, with the exact order of the scores of TLC spot sizes varying somewhat among the six different drugs. The choice of the source of β-glucuronidase appeared to be especially critical for oxymorphone, where the drug was detected only in the sample submitted to hydrolysis by the *P. vulgata* enzyme under the parameters of Experiment 1. All other enzyme preparations resulted in insufficient hydrolysis for the presence of oxymorphone to be detected. The amount of pentazocine administered to the horse (an amount considerably larger than the amounts of any of the other drugs) was sufficient to give acceptable results regardless of the source of β-glucuronidase.

The mean scores obtained with each individual drug and enzyme preparation are illustrated in FIG. 6. While hydrolysis by the *P. vulgata* preparation freed the maximum amount of drug in each case, the bovine liver β-glucuronidase hydrolyzed only 23% as much drug-glucuronide complex on the average, resulting in a mean score of 2.3. Of the five β-glucuronidase preparations tested, enzyme from *P. vulgata* in each case gave the best results, regardless of the aglycone.

Based upon the superiority of the *P. vulgata* β-glucuronidase shown in Experiment 1, the efficacy of this glucuronide hydrolysis system was tested in a situation where the efficient hydrolysis of drug-glucuronide metabolites may be forensically important. The circumstance chosen was pre-treatment of horses with furosemide (the treatment of choice for exercise-induced pulmonary hemmorhage or epistaxis). The diuresis due to furosemide can dilute out certain drugs and drug-glucuronide metabolites in urine, rendering their efficient recovery important [Tobin, "Drugs and the Performance Horse", 112–115 (1981) Charles C. Thomas, publisher, Springfield, Ill.].

In the test model, horses were treated with furosemide at 0.4 mg/kg four hours "pre-race". Four hours was selected because this is the current Kentucky rule and has been suggested by the Veterinary Chemists' Advisory Committee to the National Association of State Racing Commissioners [Gabel et al, *J. Equine Med. & Surg.* 1, 215–218 (1977)]. The test drugs were administered between 45 and 20 minutes prior to the hypothetical post time. The times of administration of the drugs were selected so that the drugs would have as maximal behavorial effects as possible at post time, and the doses selected were below threshold doses for measurable behavorial effects.

One objective of this experiment was to determine whether or not furosemide treatment would interfere with routine post-race TLC screening for drugs in horse urine. For this reason, the extraction and TLC methodology used was similar to that currently used in the Kentucky Equine Drug Testing Program. All TLC plates were coded and read "blind" by one reader to obviate observer bias in the interpretation of these tests.

In these experiments, pre-treatment of horses with furosemide did not appear to significantly reduce the detectability of any of the drugs tested. In fact, when the spot size scores were compiled and compared with the control values, the score from the furosemide-treated horses was actually statistically significantly better than in the untreated samples. Further, the reader of the plates observed that the quality of the plates from the furosemide-treated horses was superior to those from the untreated horses. It appears that the Lasix ® tends to reduce the concentration of materials which would tend to co-extract with the drug, thus leaving a "cleaner" sample. This results in less smearing and better spot definition, indicating that the drug diluting effects of these small doses of furosemide are over within three hours or less of dosing.

Since the diuretic effects of furosemide are characteristically brief, the lack of interference by these doses of furosemide with drug testing was not unexpected. However, the apparently clear-cut enhancement of the quality of the thin layer chromatograms in the presence of furosemide was surprising. In association with the fact that some drugs are not affected by diluting effects of furosemide, these results show that under some circumstances furosemide may actually enhance the detection of drugs in horse urine.

EXPERIMENTS WITH SERUM MORPHINE GLUCURONIDE

Materials and Methods

The animals, materials and methods used were generally as described above in the section entitled "MORPHINE GLUCURONIDE EXPERIMENTS". Horses were dosed with 0.1 mg of morphine per kilogram body weight. All blood samples were drawn from the right side in 20-mL Vacutainer tubes (Becton, Dickinson and Co., Rutherford, N.J.) containing no added anticoagulant. The blood samples were allowed to clot and then were centrifuged and the serum was separated off from the cellular material. Each serum sample was placed in a Centriflo ® filter (50,000 molecular weight size, obtained from Amicon Company, Lexington, Mass.) in a holder in the top of a test tube and centrifuged to afford the serum protein-free filtrate.

*Patella vulgata* β-glucuronidase (Type L-II) was obtained from Sigma Chemical Co., St. Louis, Mo., as a crude lyophilized powder and was stored at −20° C. The powder was weighed out and dissolved in distilled, de-ionized water to make solutions equivalent to 5000 U of β-glucuronidase per mL immediately before an assay was run. The pH was adjusted to 5 with acetic acid.

Hydrolysis was performed by mixing the selected quantity of serum protein-free filtrate with an equal volume of the enzyme solution and incubating in a sealed tube in a water bath at 65° C. for 3 hours. The size of serum filtrate sample employed varied from a few μL to 5 mL, depending on the length of time after dosing, with the larger samples being used when the morphine levels were expected to be low many hours after dosing.

After hydrolysis, the pH was adjusted and the solutions were analyzed as described in the foregoing "MORPHINE GLUCURONIDE EXPERIMENTS" section.

Results and Discussions

Hydrolysis of serum protein-free filtrates prepared from the serum of two horses obtained over the course of twelve hours post morphine administration indicated a substantial fraction of serum morphine was in the form of morphine glucuronide (FIG. 7). The morphine glucuronide appeared shortly after dosing. By 5 minutes post dosing, 65% of the morphine in the blood was in the form of conjugated morphine. In another study involving 4 horses, only 3 minutes after dosing, 16% of the serum morphine was found as the glucuronide conjugate. Between 5 minutes and 12 hours post dosing, hydrolysis of serum protein-free filtrate resulted in an average 4.9-fold increase in free morphine levels. As serum morphine dropped to very low levels (less than 1 or 2 ng/mL), the fraction bound to glucuronic acid decreased, until little or no morphine glucuronide was observed 48 hours after dosing.

While the invention has been described in terms of various preferred embodiments, the skilled artisan will appreciate that various modifications, substitutions, omissions and additions may be made without departing from the spirit thereof. Accordingly, it is intended that the scope of the present invention be limited solely by the scope of the following claims.

What is claimed is:

1. A method for hydrolyzing glucuronides in a sample of mammalian body fluid, said glucuronides being derived from a narcotic analgesic, antagonist or agonist-antagonist whose metabolism includes conjugation with glucuronic acid, said method comprising incubating said sample with a glucuronide hydrolyzing effective amount of *Patella vulgata* β-glucuronidase, at from about 60 to about 70° C. for a period of time of at least about 1 hour, to effect enzymatic hydrolysis of glucuronides present therein.

2. A method for increasing the sensitivity of a chromatographic technique for detecting the administration to a mammal of a narcotic analgesic, antagonist or agonist-antagonist whose metabolism includes conjugation with glucuronic acid, said method comprising incubating a sample of mammalian body fluid with an amount of *Patella vulgata* β-glucuronidase sufficient to hydrolyze glucuronides present therein, at a temperature of from about 60° to 70° C. for a period of time of at least about 1 hour, and thereafter subjecting the incubated sample to chromatography.

3. A method according to claim 1 or 2, wherein about 5000 U of *Patella vulgata* β-glucuronidase are employed per milliliter of body fluid sample.

4. A method according to claim 1 or 2, wherein the incubation is conducted at a temperature of about 65° C.

5. A method according to claim 1 or 2, wherein the incubation is conducted for a period of time of from about 1 to about 6 hours.

6. A method according to claim 1 or 2, wherein the incubation is conducted for a period of time of from about 1 to 4 hours.

7. A method according to claim 1 or 2, wherein the incubation is conducted for a period of time of from about 1 to about 3 hours.

8. A method according to claim 1 or 2, wherein the incubation is conducted for a period of time of about 1 hour.

9. A method according to claim 1 or 2, wherein the incubation is conducted for a period of time of about 3 hours.

10. A method according to claim 1 or 2, wherein the incubation is conducted at a pH of from about 4.5 to about 5.5.

11. A method according to claim 1 or 2, wherein the incubation is conducted at a pH of about 5.

12. A method according to claim 1 or 2, wherein the *Patella vulgata* β-glucuronidase is employed as an aqueous solution prepared from crude lyophilized *P. vulgata* powder and water.

13. A method according to claim 12, wherein said aqueous solution of *Patella vulgata* β-glucuronidase has an enzyme concentration of about 5000 U/mL.

14. A method according to claim 13, wherein said aqueous solution of *Patella vulgata* β-glucuronidase is employed in equal volume to the body fluid sample to be incubated.

15. A method according to claim 1 or 2, wherein the body fluid sample is a mammalian urine sample.

16. A method according to claim 1 or 2, wherein the body fluid sample is a mammalian blood or plasma sample.

17. A method according to claim 1 or 2, wherein the body fluid sample is a mammalian serum sample.

18. A method according to claim 1 or 2, wherein the body fluid sample is a sample of mammalian serum protein-free filtrate.

19. A method according to claim 1 or 2, wherein the body fluid sample is an equine urine sample.

20. A method according to claim 1 or 2, wherein the body fluid sample is a sample of equine serum protein-free filtrate.

21. A method according to claim 2, wherein the incubated sample is subjected to thin layer chromatography.

22. A method according to claim 2, wherein the incubated sample is subjected to gas-liquid chromatography.

23. A method according to claim 1 or 2, wherein said narcotic analgesic, antagonist or agonist-antagonist is morphine.

24. A method according to claim 23, wherein the body fluid sample is an equine urine sample.

25. A method according to claim 23, wherein the body fluid sample is a sample of equine serum protein-free filtrate.

26. A method according to claim 1 or 2, wherein said narcotic analgesic, antagonist or agonist-antagonist is apomorphine, butorphanol, hydromorphone, nalbuphine, oxymorphone or pentazocine.

27. A method according to claim 26, wherein said narcotic analgesic, antagonist or agonist-antagonist is apomorphine.

28. A method according to claim 26, wherein said narcotic analgesic, antagonist or agonist-antagonist is butorphanol.

29. A method according to claim 26, wherein said narcotic analgesic, antagonist or agonist-antagonist is hydromorphone.

30. A method according to claim 26, wherein said narcotic analgesic, antagonist or agonist-antagonist is nalbuphine.

31. A method according to claim 26, wherein said narcotic analgesic, antagonist or agonist-antagonist is oxymorphone.

32. A method according to claim 26, wherein said narcotic analgesic, antagonist or agonist-antagonist is pentazocine.

33. A method according to claim 26, wherein the body fluid sample is an equine urine sample.

34. A method according to claim 26, wherein the body fluid sample is a sample of equine serum protein-free filtrate.

35. A method according to claim 1 or 2, wherein said narcotic analgesic, antagonist or agonist-antagonist is etorphine, diprenorphine, nalorphine, levorphanol, buprenorphine or heroin.

36. A method according to claim 35, wherein the body fluid sample is a sample of equine urine or equine serum protein-free filtrate.

37. A method according to claim 1 or 2, wherein said narcotic analgesic, antagonist or agonist-antagonist is cyclazocine, phenazocine, levallorphan, naloxone, naltrexone, alazocine or oxilorphan.

* * * * *